United States Patent [19]

Kurz

[11] 4,277,236
[45] Jul. 7, 1981

[54] ORTHODONTIC INSTRUMENT FOR APPLYING ELASTIC LIGATURES

[76] Inventor: Craven H. Kurz, 10921 Wilshire Blvd., Suite 512, Los Angeles, Calif. 90024

[21] Appl. No.: 135,976
[22] Filed: Mar. 31, 1980
[51] Int. Cl.$^3$ ............................................ A61C 3/00
[52] U.S. Cl. .................................. 433/3; 221/312 A
[58] Field of Search .................... 433/3; 221/312 A

[56] References Cited

U.S. PATENT DOCUMENTS

| 3,134,168 | 5/1964 | Erdmann | 221/312 A |
| 3,137,932 | 6/1964 | Erdmann | 221/312 A |
| 3,458,031 | 7/1969 | Hoffman | 433/3 |
| 3,861,045 | 1/1975 | Canter et al. | 433/3 |
| 4,040,187 | 8/1977 | Cardena | 433/3 |

FOREIGN PATENT DOCUMENTS 2808149  5/1979  Fed. Rep. of Germany .............. 433/3

Primary Examiner—Gene Mancene
Assistant Examiner—John J. Wilson
Attorney, Agent, or Firm—Keith D. Beecher

[57] ABSTRACT

An orthodontic instrument is provided to permit the application of arch wire retaining elastic annular ligatures to orthodontic brackets on the labial surface of the teeth of a patient. The instrument includes a disposable cartridge which is loaded with a stack of the annular elastic ligatures, and which serves as a dispenser member, a housing for receiving the cartridge, a spring-biased pusher member slidably mounted in the housing and engaging the rear ligature of the stack to push the stack toward the forward end of the cartridge, so that the forward ligature moves along an enlarged end portion of the cartridge, a plurality of push rods extending along the cartridge under the ligatures with the ends of the push rods engaging the forward ligature, and release means for moving the cartridge reciprocally with respect to the housing so that the forward ligature may be forced over the enlarged end of the cartridge by the push rods each time the instrument is operated.

3 Claims, 5 Drawing Figures

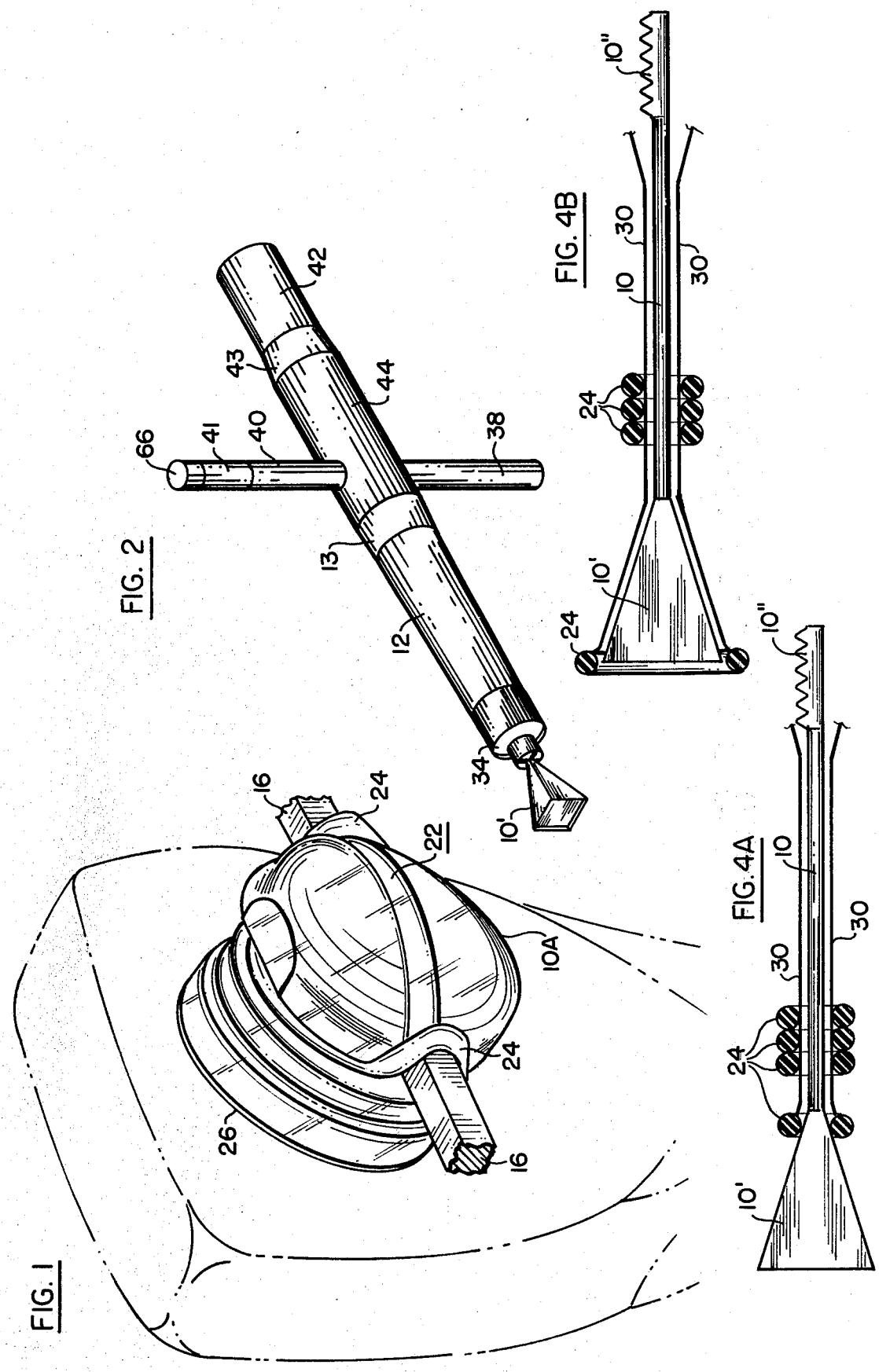

ORTHODONTIC INSTRUMENT FOR APPLYING ELASTIC LIGATURES

BACKGROUND

In the past, the application of the usual small annular elastic arch wire supporting ligatures to the orthodontic brackets in the mouth of the patient has been a tedious and time consuming operation. Usually the ligatures are applied by hand and by the use of forceps or similar instruments to stretch the ligatures and to insert the ligatures into the annular support grooves in the brackets. The objective of the present invention is to provide a simple hand tool by which such elastic ligatures may be applied simply and expeditiously in a stretched condition into the annular grooves in the orthodontic brackets and around the arch wire, so that the arch wire may be supported on the brackets.

BRIEF DESCRIPTION OF THE DRAWINGS

FIG. 1 is a perspective representation of an orthodontic bracket supported on the tooth of a patient, and an arch wire supported on the bracket by an annular elastic ligature;

FIG. 2 is a perspective view of the instrument of the invention in one of its embodiments;

FIGS. 4A and 4B are views of certain operating components of the instrument in two operational positions and are useful in explaining the operation of the instrument.

DETAILED DESCRIPTION OF THE ILLUSTRATED EMBODIMENT

Figure 3:
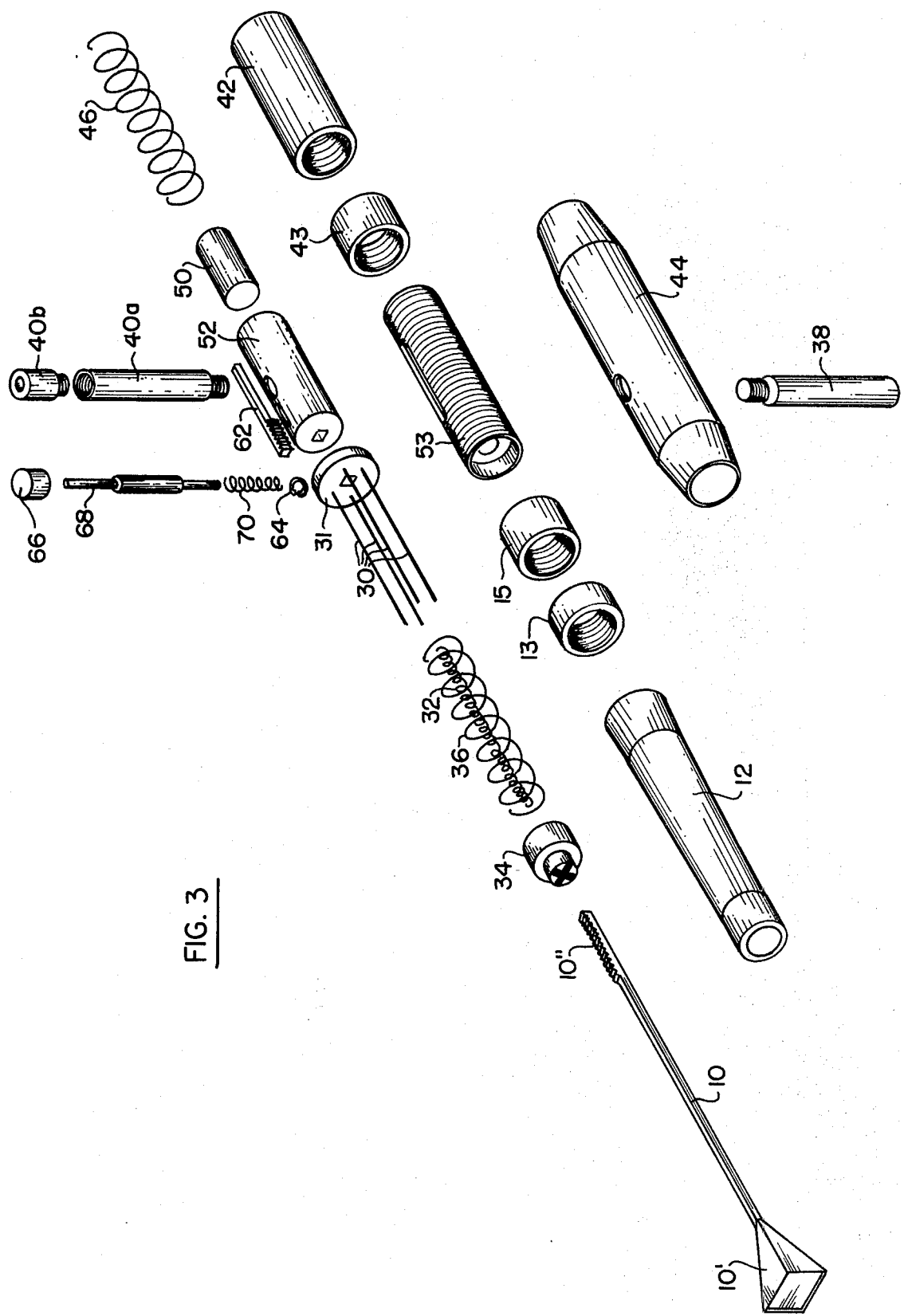
FIG. 3 is a perspective exploded view of the instrument of FIG. 2.

The orthodontic bracket is designated 10A in FIG. 1, and it receives an arch wire 16. The arch wire 16 is received in a slot 22 on the bracket. The bracket has a peripheral groove which receives an annular elastic ligature 24 which serves to support the arch wire on the bracket. The bracket is affixed to the labial surface of the tooth by an adhesive layer 26. It is to be understood, of course, that the particular orthodontic bracket shown in FIG. 1 is shown merely by way of example, and it will be evident as the description proceeds that the instrument of the invention may be used to apply elastic annular ligatures to any type of orthodontic bracket.

As shown in FIGS. 2 and 3, the instrument of the invention includes a trumpet-shaped removable and disposable cartridge 10 which serves as a dispenser member, and which is slidably received in an elongated shroud 12 for reciprocal movement within the shroud and along the longitudinal axis thereof. The ligatures 24 are stacked adjacent to one another along the cartridge 10, as shown in FIGS. 4A and 4B. Cartridge 10 has an enlarged end section designated 10' which has a flared, "trumpet" configuration. The forward extremity of the end section 10' is shaped to conform with the configuration of the particular bracket 10A with which the instrument is used, so that the ligatures may be easily and conveniently applied to the bracket.

Four push wires 30 are mounted on a seat 31 within the shroud 12, and the push wires extend along cartridge 10, and they are held in place by a helical spring 36. The rear ends of the push wires are attached to the seat 31, so that the wires move with the housing.

A piston 52 is mounted within a housing 53 in coaxial relationship with the shroud 12, and the piston engages the seat 31. Housing 53 is attached to shroud 12 by nuts 13 and 15. A second helical spring 32 is mounted in the shroud 10 in coaxial relationship with the cartridge 10, and spring 32 bears against a plunger 34, to bias the plunger against the stack of ligatures on the cartridge 10.

When the instrument is in its released condition, the push wires 30 pass under the ligatures on the cartridge 10, but engage the forward ligature, as shown in FIG. 4A. The forward ligature is forced partially along the enlarged end section 10' by the plunger 34. Then, when the instrument is operated, the cartridge 10 is pulled toward the rear of the instrument, so that the wires 30 move the forward ligature 24 along the enlarged end section 10' and displace the ligature over the extremity of the end section 10', as shown in FIG. 4B, in a stretched condition. The stretched ligature is then received by the annular groove in the bracket 24 of FIG. 1, to assume the position shown in FIG. 1 in which it supports the arch wire 16 on the bracket.

The cartridge 10 is drawn towards the rear of the instrument by a pair of radial handles 38, 40a and 40b which are grasped by the orthodontist, and which are pulled toward the right in FIG. 2, as a butt member 42 is held stationary, for example, by the palm of the operator, so that the cartridge 10 and a tubular slide member 44 may be moved to the right in FIG. 2, as the shroud 12 is held stationary.

The butt 42 is attached to housing 53, together with an alignment nut 43. When butt 42 is held, and the handles 38 and 40 are moved to the right in FIG. 2, piston 52 and a spring guide 50 are moved against the force of a spring 46, until the guide 50 engages the inner end of butt 42. During that action, the cartridge 10 is moved to the right of FIG. 2, so that the forward ligature may be dispensed onto bracket 10A of FIG. 1 by push wires 30, as shown in FIG. 4B. Then, when the handles are released, cartridge 10 moves from the position shown in FIG. 4B to the position shown in FIG. 4A, and is in position to release the next ligature, when the instrument is next operated.

As shown in FIGS. 3, 4A and 4B, the cartridge 10 has a serrated section 10" at its rear end which is engaged by a serrated member 62 in the internal housing 52. The serrated member 62 is normally biased into engagement with the serrated section 10" by a wishbone spring 64 mounted in the housing 53. To release the cartridge, a pushbutton 66 is pushed so that pin 68 may move against the bias of a spring 70 against the member 62 to disengage the member from the cartridge 10, permitting the cartridge to be removed from the forward end of housing 12, and to be replaced by a new loaded cartridge, when the original cartridge is empty.

Accordingly, to load the instrument, a cartridge 10 preloaded with a stack of ligatures 24 is inserted into the end of a shroud 12 and through a central opening in plunger 34 until it is locked with piston 52 by ratchet 62.

Then, to operate the instrument, the instrument is held so that butt 52 nests against the palm of the hand of the operator whose fingers are wrapped around handles 38, 40a, 40b. The front end of cartridge 10 is then placed against bracket 10a of FIG. 1. Then by pulling the handles, the piston 52 and cartridge 10 remain stationary while the push wires move forward from the position of FIG. 3A to the position of FIG. 3B along grooves in the cartridge to push the forward ligature 24 from the base to the end of the trumpet-shaped portion 10', so that the ligature may be disposed in expanded form over the end of portion 10' and onto bracket 10A of FIG. 1.

Then, if the pressure on the butt 42 is released, return spring 46 and piston 52 will return the push wires 30 to the position shown in FIG. 4A.

When all the ligatures on cartridge 10 have been dispensed, the pushbutton 66 may be depressed, as noted, to release the cartridge and to permit it to be replaced with a new, loaded cartridge.

The instrument of the present invention, as described above, is relatively simple and inexpensive in its construction, and it is easy to use. Also, when a cartridge within the instrument becomes empty, it may easily be replaced by a new loaded cartridge.

It will be appreciated that while a particular embodiment of the invention has been shown and described, modifications may be made. It is intended in the claims to cover all modifications which come within the spirit and scope of the invention.

What is claimed is:

1. An orthodontic instrument for applying annular elastic ligatures to brackets on the teeth of a patient for retaining the arch wire on the brackets, said instrument comprising: an elongated housing having a forward end and a rear end; an elongated dispenser member received in said housing for reciprocal movement therein along the longitudinal axis thereof, said dispenser member having an enlarged end at the forward end of the housing; a plurality of annular elastic ligatures stacked adjacent to one another on said dispenser member in coaxial relationship therewith, a pusher member slidably mounted in said housing in coaxial relationship with said dispenser member and in position to engage the rear ligature of the stack on said dispenser member; resilient means biasing the pusher member toward the forward end of the housing to move the forward ligature of the stack partially along the enlarged end of the dispenser member; manually operable release means engaging the forward ligature to force the forward ligature along the enlarged end of the dispenser member and over the extremity thereof, said release means comprising a plurality of push rods extending axially along the dispenser member under the ligature therein toward said enlarged end of said dispenser member, and manually operable means for moving said dispenser member axially with respect to the housing towards the rear end of the housing to cause said push rods to move forward relative to said dispenser member so as to move the forward ligature along the enlarged end of the dispenser and over the extremity thereof.

2. The orthodontic instrument defined in claim 1, and which includes resilient means engaging said manually operable means to move the dispenser member towards the forward end of the housing when the manually operable means is released to cause the pusher rods to move back relative to said dispenser member until the ends of the rods engage the next forward ligature in the stack.

3. The orthodontic instrument defined in claim 1, and which includes release means mounted in said housing for enabling said dispenser member to be removed from the housing after all the ligatures thereon have been dispensed and to be replaced by a new dispenser member loaded with a new stack of ligatures.

* * * * *